United States Patent
Kang et al.

(10) Patent No.: US 7,714,173 B2
(45) Date of Patent: May 11, 2010

(54) METHOD FOR PURIFYING TEREPHTHALALDEHYDE

(75) Inventors: Seong-Hoon Kang, Daejeon (KR); In-Kyu Park, Daejeon (KR); Jong-Suh Park, Gongju-si (KR); Young-Dae Kim, Daejeon (KR); Jong-Hyun Chae, Daejeon (KR)

(73) Assignee: LG Chem, Ltd., Seoul (KR)

( * ) Notice: Subject to any disclaimer, the term of this patent is extended or adjusted under 35 U.S.C. 154(b) by 0 days.

(21) Appl. No.: 12/308,714

(22) PCT Filed: Jun. 14, 2007

(86) PCT No.: PCT/KR2007/002893

§ 371 (c)(1),
(2), (4) Date: Aug. 21, 2009

(87) PCT Pub. No.: WO2008/002028

PCT Pub. Date: Jan. 3, 2008

(65) Prior Publication Data

US 2010/0048958 A1 Feb. 25, 2010

(30) Foreign Application Priority Data

Jun. 29, 2006 (KR) .................. 10-2006-0059438

(51) Int. Cl.
*C07C 45/81* (2006.01)

(52) U.S. Cl. .................. 568/437; 568/438
(58) Field of Classification Search .......... 568/437, 568/438
See application file for complete search history.

(56) References Cited

U.S. PATENT DOCUMENTS

| 2,888,488 | A | * | 5/1959 | Nace .................. 568/437 |
| 4,174,352 | A | | 11/1979 | Fisher et al. |
| 4,297,519 | A | | 10/1981 | Ertel |
| 4,579,977 | A | | 4/1986 | Drake |
| 4,978,802 | A | | 12/1990 | Campo et al. |
| 6,437,176 | B2 | | 8/2002 | Matsuoka et al. |

\* cited by examiner

*Primary Examiner*—Sikarl A Witherspoon
(74) *Attorney, Agent, or Firm*—McKenna Long & Aldridge LLP

(57) ABSTRACT

The present invention relates to a method for preparing high-purity terephthalaldehyde which comprises re-crystallizing terephthalaldehyde crystals containing impurities, using an anti-solvent. Specifically, the present invention relates to a method for preparing terephthalaldehyde which comprises dissolving low-purity terephthalaldehyde prepared by a conventional method in dimethylsulfoxide and then re-crystallizing the solution, using water as an anti-solvent. The present invention is not only environment-friendly because it uses water only as an anti-solvent, but also economical because it may simply prepare high-purity terephthalaldehyde in a short time.

6 Claims, 1 Drawing Sheet

METHOD FOR PURIFYING TEREPHTHALALDEHYDE

This application claims priority to PCT/KR2007/002893 filed on Jun. 14, 2007 and also Korean Patent Application No. 10-2006-0059438 filed on Jun. 29, 2006, the contents of which are hereby incorporated by reference in their entirety.

TECHNICAL FIELD

The present invention relates to a method for purifying terephthalaldehyde. Specifically, the present invention relates to a method for purifying terephthalaldehyde which comprises adding an anti-solvent to terephthalaldehyde dissolved in dimethylsulfoxide as a solvent to precipitate a high purity terephthalaldehyde.

BACKGROUND ART

Aromatic aldehydes have aldehyde groups with a high reactivity, so that they may be employed in a wide variety of uses. Especially, terephthalaldehydes having two aldehyde groups at para-positions as Formula 1 below are noted for basic raw materials such as medicinal products, agrichemicals, pigments, liquid crystal polymers, electro-conductive polymers, and heat-resistant plastics.

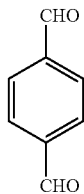

1

Said terephthalaldehyde of Formula 1 is a sublimable white solid having a molecular weight of 134.13 and a melting point of 114-116° C. It is known that it is well dissolved in alcohols, and is also dissolved in ethers, alkali solutions and hot water.

Terephthalaldehyde as a raw material of the present invention is prepared by the known methods.

Methods for preparing terephthalaldehyde used as a raw material in the present invention are briefly described as follows:

In the methods for preparing terephthalaldehyde, there is a method for dehydrating intermediates obtained via chlorination, a method for hydrogenating methylterephthalate, or a method for preparing terephthalate by oxidating p-xylene in vapor phase, etc.

In order to use terephthalaldehyde as a raw material in a polymer synthesis or a fine chemical process, it should be purified to a high purity, for which impurities contained in terephthalaldehyde, such as benzaldehyde, p-toluadldehyde, 4-hydroxybenzaldehyde and the like, have to be removed.

Until now, there is almost no example reported for the method for preparing a high purity terephthalaldehyde which may be used in the polymer synthesis or the fine chemical process by efficiently removing impurities produced in the synthesis of terephthalaldehyde.

U.S. Pat. No. 2,888,488 discloses a method for preparing terephthalaldehyde which includes solvent extracting—drying—subliming as a purification process. This method has, however, problems that its procedures are complicated and a non-environment friedly compound, chloroform, is used as a solvent.

JP Unexamined Patent Publication No. 2001-199910 discloses a method for re-crystallizing aromatic alehdydes by a cooling process. This method is also limited to obtaining a high purity terephthalaldehyde.

DISCLOSURE OF THE INVENTION

The object of the present invention is intended to solve the problems above, and is to provide a method for preparing terephthalaldehyde which comprises dissolving a low-purity terephthalaldehyde, including terephthalaldehyde and a small quantity of impurities obtained through a conventional method, in dimethylsulfoxide (DMSO) and then re-crystallizing the solution with an anti-solvent.

The present invention relates to a method for purifying terephthalaldehyde which comprises the steps of dissolving terephthalaldehyde crystals, containing impurities, in dimethylsulfoxide and then re-crystallizing the solution, using an anti-solvent.

The present invention is explained in detail below.

The impurity-containing crude terephthalaldehydes used herein are not specifically limited, and include terephthalaldehydes which are prepared by the known methods or commercially available terephthalaldehydes.

In a method for purifying terephthalaldehyde which comprises dissolving crude terephthalaldehyde in a solvent and then re-crystallizing the solution, using an anti-solvent, the present invention is characterized by using dimethylsulfoxide as the solvent. In the method for purifying terephthalaldehyde according to the present invention, usual alcohols or ethers may be used as a solvent dissolving terephthalaldehyde. However, dimethylsulfoxide according to the present invention has more excellent solubility of terephthalaldehyde and major impurities than those of the alcohols or the ethers, and may prepare terephthalaldehyde in a higher yield and purity. In addition, when alcohols such as methanol are used, terephthalaldehyde is changed into a material such as acetal. But such change is not occurred in dimethylsulfoxide, so that the present invention has an excellent stability.

The amount of dimethylsulfoxide is not limited, but is preferably contained in a range adjacent to a solubility that terephthalaldehyde crystals are dissolved In addition, if an anti-solvent herein is a solvent with a low solubility of terephthalaldehyde which may be mixed with dimethylsulfoxide, it may be used without any limitation. Fore example, water, hydrocarbons or aromatic solvents may be used. Especially, considering the side of environment, it is preferred to use water. Said water includes, but not limited to, distilled water and de-ionized water as purified water.

The physical properties of dimethylsulfoxide and water as solvents used herein, and their solubility of terephthalaldehyde and major impurities are represented in Table 1 below.

TABLE 1

|  |  | $H_2O$ | DMSO |
|---|---|---|---|
| Property | Specific Gravity | 1 | 1.1 |
|  | Boiling Point (° C.) | 100 | 189 |
|  | Melting Point (° C.) | 0 | 18.4 |
|  | Solubility in Water | — | miscible |
| Solubility | 4-CBA | <1.67 | 1000 |
|  | 4-HBA | 2.5 | 1000 |
|  | TPA | <1.67 | 50 |
|  | BA | <1.67 | 500 |

TABLE 1-continued

|  | H$_2$O | DMSO |
| --- | --- | --- |
| HQ | 20 | 1000 |
| Crude TPAL | 10 | 200 |
| Ald. TPAL | 10 | 200 |

Unit of solubility: g/L, measured at 25° C.
[p-tolualdehyde (PTAL) and benzaldehyde (BAL) are in liquid at room temperature]
4-CBA: 4-carboxybenzaldehyde
4-HBA: 4-hydroxybenzaldehyde
TPA: terphthalic acid
BA: benzoic acid
HQ: hydroquinone
crude TPAL: pre-purified terephthalaldehyde
Ald. TPAL: Aldrich agent terephthalaldehyde The amounts of dimethylsulfoxide and anti-solvent may be used by appropriately regulating them depending on the yield of terephthalate. Especially, when dimethylsulfoxide according to the present invention is used, the anti-solvent can be used in a smaller quantity, over using an alcohol as a solvent. In particular, a weight ratio of anti-solvent to dimethylsulfoxide is preferably 0.05~4:1, and more preferably 0.1~3:1.

If the weight ratio of anti-solvent:dimethylsulfoxide is less than 0.05, the yield may be lowered, whereas if the ratio is more than 4, the waste water may be increased.

Meanwhile, a method of using said anti-solvent is not specifically limited. That is, an anti-solvent may be added or added dropwise to a solution of dimethylsulfoxide in which tetraphthalaldehyde is dissolved, or a solution of dimethylsulfoxide in which tetraphthalaldehyde is dissolved may be added or added dropwise to an anti-solvent. Preferably, the present invention comprises adding an anti-solvent to a solution of dimethylsulfoxide in which crude terephthalaldehyde is dissolved, and then re-crystallizing terephthalaldehyde 10 minutes to 2 hours after leaving the solution as such. At this time, its re-crystallization temperature is not specifically limited, but is preferably performed in a range of about 15~60° C.

The re-crystallized terephthalaldehyde as above may be filtered and dried to afford the finally re-crystallized terephthalaldehyde. At this time, drying may be practiced using a usual drying method such as an oven drying or a vacuum drying, with appropriately regulating temperature and time of drying. Especially, it is preferred to dry at 60 to 80° C. for 20 to 28 hours.

In addition, when the desired terephthalaldehyde is in high purity, the step of purifying terephthalaldehyde as above may be, of course, repeated two or more times.

BEST MODE FOR CARRYING OUT THE INVENTION

Figure 1:
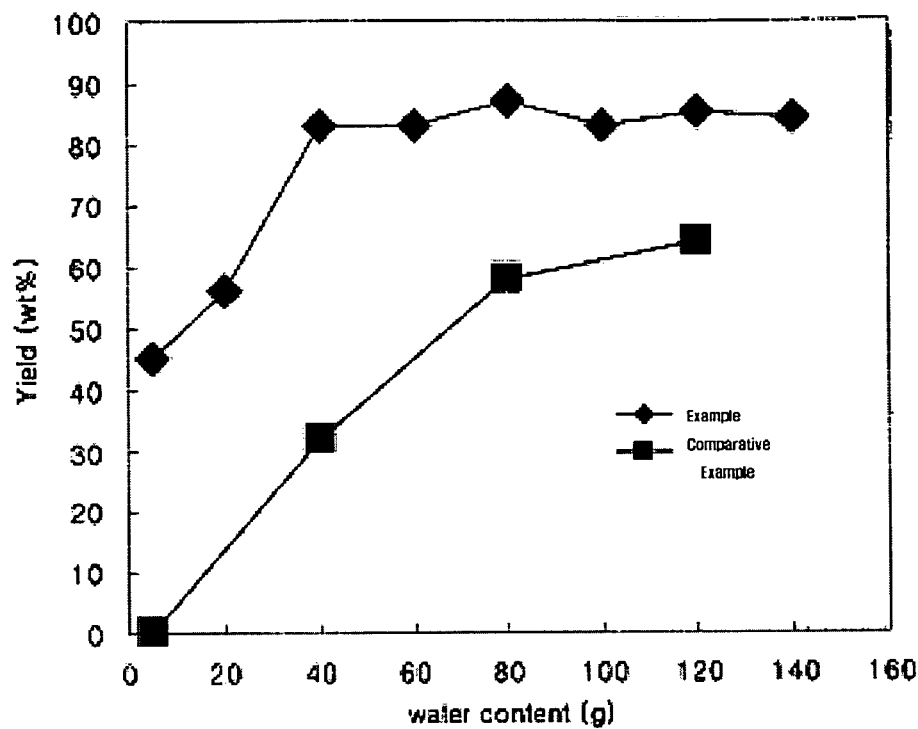
FIG. 1 is a graph depicting yields of TPAL according to examples and comparative examples of the present invention.
Figure 2:
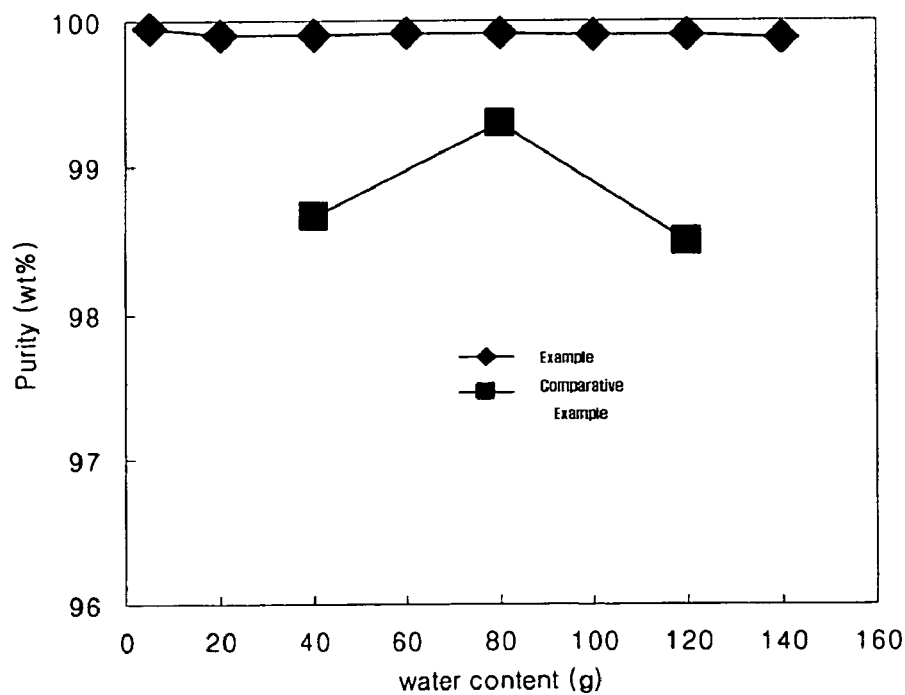
FIG. 2 is a graph depicting purity of TPAL according to examples and comparative examples of the present invention.

To assist understanding of the present invention, the preferred examples are shown below. However, these examples are intended to illustrate the present invention, whose scope is not limited to these examples.

EXAMPLES

Example 1

5 g of pre-purified terephthalaldehyde was added to 50 g of dimethylsulfoxide and completely dissolved, with well stirring at room temperature. To the solution was added 5 g of water used as an anti-solvent (weight ratio of water to dimethylsulfoxide=0.1:1). After adding water, terephthalaldehyde was re-crystallized and then left to stand at room temperature for 1 hour. The resulting product was filtered and dried at 70° C. for 24 hours to obtain the re-crystallized terephthalaldehyde.

Purities of terephthalaldehyde before and after purification were measured by a gas chromatography with mass selective detector (GC-MSD). Terephthalaldehyde used in purification was identified to be a purity of 97.9 wt % by GC-MSD. In the following examples, terephthalaldehyde with the same purity was used and purified.

Purity and yield of terephthalaldehyde after purification were represented in Table 2 below.

Example 2

Terephthalaldehyde was purified by the same method as Example 1 except that 20 g of water was added as an anti-solvent (weight ratio of water to dimethylsulfoxide=0.4:1). Purity of the obtained terephthalaldehyde was determined by GC-MSD. Purity and yield of terephthalaldehyde were represented in Table 2 below.

Example 3

Terephthalaldehyde was purified by the same method as Example 1 except that 40 g of water was added as an anti-solvent (weight ratio of water to dimethylsulfoxide=0.8:1). Purity of the obtained terephthalaldehyde was determined by GC-MSD. Purity and yield of terephthalaldehyde were represented in Table 2 below.

Example 4

Terephthalaldehyde was purified by the same method as Example 1 except that 60 g of water was added as an anti-solvent (weight ratio of water to dimethylsulfoxide=1.2:1). Purity of the obtained terephthalaldehyde was determined by GC-MSD. Purity and yield of terephthalaldehyde were represented in Table 2 below.

Example 5

Terephthalaldehyde was purified by the same method as Example 1 except that 80 g of water was added as an anti-solvent (weight ratio of water to dimethylsulfoxide=1.6:1).

Purity of the obtained terephthalaldehyde was determined by GC-MSD. Purity and yield of terephthalaldehyde were represented in Table 2 below.

Example 6

Terephthalaldehyde was purified by the same method as Example 1 except that 100 g of water was added as an anti-solvent (weight ratio of water to dimethylsulfoxide=2:1). Purity of the obtained terephthalaldehyde was determined by GC-MSD. Purity and yield of terephthalaldehyde were represented in Table 2 below.

Example 7

Terephthalaldehyde was purified by the same method as Example 1 except that 120 g of water was added as an anti-solvent (weight ratio of water to dimethylsulfoxide=2.4:1). Purity of the obtained terephthalaldehyde was determined by GC-MSD. Purity and yield of terephthalaldehyde were represented in Table 2 below.

Example 8

Terephthalaldehyde was purified by the same method as Example 1 except that 140 g of water was added as an anti-solvent (weight ratio of water to dimethylsulfoxide=2.8:1). Purity of the obtained terephthalaldehyde was determined by GC-MSD. Purity and yield of terephthalaldehyde were represented in Table 2 below.

Comparative Example 1

5 g of pre-purified terephthalaldehyde was added to 50 g of methanol and completely dissolved, with well stirring at room temperature. To the solution was added 5 g of water used as an anti-solvent (weight ratio of water to methanol=0.1:1). After adding water, terephthalaldehyde was re-crystallized and then left to stand at room temperature for 1 hour. The resulting product was filtered and dried at 70° C. for 24 hours to obtain the re-crystallized terephthalaldehyde.

Comparative Example 2

Terephthalaldehyde was purified by the same method as Comparative Example 1 except that 40 g of water was added as an anti-solvent (weight ratio of water to methanol=0.8:1). Purity of the obtained terephthalaldehyde was determined by GC-MSD. Purity and yield of terephthalaldehyde were represented in Table 2 below.

Comparative Example 3

Terephthalaldehyde was purified by the same method as Comparative Example 1 except that 80 g of water was added as an anti-solvent (weight ratio of water to methanol=1.6:1). Purity of the obtained terephthalaldehyde was determined by GC-MSD. Purity and yield of terephthalaldehyde were represented in Table 2 below.

Comparative Example 4

Terephthalaldehyde was purified by the same method as Comparative Example 1 except that 120 g of water was added as an anti-solvent (weight ratio of water to methanol=2.4:1). Purity of the obtained terephthalaldehyde was determined by GC-MSD. Purity and yield of terephthalaldehyde were represented in Table 2 below.

TABLE 2

| Class | Anti-solvent | Solvent | Anti-solvent:solvent | Yield of TPAL (%) | Purity after Purification (%) |
| --- | --- | --- | --- | --- | --- |
| Exam. 1 | Water (5 g) | DMSO | 0.1:1 | 45 | 99.95 |
| Exam. 2 | Water (20 g) | DMSO | 0.4:1 | 56 | 99.9 |
| Exam. 3 | Water (40 g) | DMSO | 0.8:1 | 83 | 99.9 |
| Exam. 4 | Water (60 g) | DMSO | 1.2:1 | 83 | 99.91 |
| Exam. 5 | Water (80 g) | DMSO | 1.6:1 | 87 | 99.91 |
| Exam. 6 | Water (100 g) | DMSO | 2:1 | 83 | 99.9 |
| Exam. 7 | Water (120 g) | DMSO | 2.4:1 | 85 | 99.9 |
| Exam. 8 | Water (140 g) | DMSO | 2.8:1 | 84 | 99.88 |
| Comp. Exam. 1 | Water (5 g) | Methanol | 0.1:1 | 0.3 | —* |
| Com. Exam. 2 | Water (40 g) | Methanol | 0.8:1 | 32 | 98.66 |
| Com. Exam. 3 | Water (80 g) | Methanol | 1.6:1 | 58 | 99.29 |
| Com. Exam. 4 | Water (120 g) | Methanol | 2.4:1 | 64 | 98.49 |

*In Comparative Example 1, purity cannot be measured, since the recovered amount is insufficient.

As shown in Table 2 above, it can be identified that terephthalaldehyde with higher yield and purity may be obtained, even if a small quantity of water is used, in Examples 1 to 8 using dimethylsulfoxide as a solvent and water as an anti-solvent to be subjected to purification, according to the present invention, over Comparative Examples 1 to 4 using methanol as a solvent.

INDUSTRIAL APPLICABILITY

In the method for purifying terephthalaldehyde according to the present invention, high purity terephthalaldehyde may be prepared by dissolving terephthalaldehyde in dimethylsulfoxide and then using water as an anti-solvent. In addition, the preparation method is simple and environmentally preferred, since water is used as an anti-solvent, and thus high purity terephthalaldehyde may be economically purified.

The above description is explained in detail only about embodiments of the present invention. However, it is apparent to one skilled in this field that various modifications and changes are available within the technical concepts of the present invention. Such modifications and changes should be fallen within the appended claims.

The invention claimed is:

1. A method for purifying terephthalaldehyde which comprises the steps of dissolving terephthalaldehyde crystals containing impurities in dimethylsulfoxide and then re-crystallizing the solution, using an anti-solvent.

2. The method for purifying terephthalaldehyde of claim 1, which is characterized by using water as the anti-solvent.

3. The method for purifying terephthalaldehyde of claim 1, which is characterized in that the weight ratio of said anti-solvent to dimethylsulfoxide is 0.05~4:1.

4. The method for purifying terephthalaldehyde of claim 1, which is characterized in that the weight ratio of said anti-solvent to dimethylsulfoxide is 0.1~3:1.

5. The method for purifying terephthalaldehyde of claim 1, wherein the step of re-crystallizing the solution using the anti-solvent comprises adding the anti-solvent to the dimethylsulfoxide solution in which terephthalaldehyde is dissolved, and leaving to stand for 10 minutes to 2 hours.

6. The method for purifying terephthalaldehyde of claim 1, which further comprises a step of filtering and drying the re-crystallized terephthalaldehyde.

* * * * *